US011497579B2

(12) United States Patent
Lacy et al.

(10) Patent No.: US 11,497,579 B2
(45) Date of Patent: Nov. 15, 2022

(54) POLE CLAMP ASSEMBLY FOR MEDICAL DEVICES

(71) Applicant: Smiths Medical ASD, Inc., Plymouth, MN (US)

(72) Inventors: Christopher Allen Lacy, Arden Hills, MN (US); Kevin Krautbauer, St. Paul, MN (US); Steven Plager, Eden Prairie, MN (US)

(73) Assignee: Smiths Medical ASD, Inc., Plymouth, MN (US)

( * ) Notice: Subject to any disclaimer, the term of this patent is extended or adjusted under 35 U.S.C. 154(b) by 145 days.

(21) Appl. No.: 16/481,344

(22) PCT Filed: Apr. 18, 2018

(86) PCT No.: PCT/US2018/028093
§ 371 (c)(1),
(2) Date: Jul. 26, 2019

(87) PCT Pub. No.: WO2018/195154
PCT Pub. Date: Oct. 25, 2018

(65) Prior Publication Data

US 2020/0000546 A1 Jan. 2, 2020

Related U.S. Application Data

(60) Provisional application No. 62/487,189, filed on Apr. 19, 2017.

(51) Int. Cl.
*A61B 90/57* (2016.01)
*A61M 5/14* (2006.01)

(52) U.S. Cl.
CPC ........... *A61B 90/57* (2016.02); *A61M 5/1415* (2013.01); *A61B 2090/571* (2016.02); *A61M 2209/082* (2013.01)

(58) Field of Classification Search
USPC .................. 248/230.6, 231.71, 316.1, 316.4
See application file for complete search history.

(56) References Cited

U.S. PATENT DOCUMENTS

| | | |
|---|---|---|
| 4,511,158 A | 4/1985 | Varga et al. |
| 4,756,706 A | 7/1988 | Kerns et al. |

(Continued)

FOREIGN PATENT DOCUMENTS

| | | |
|---|---|---|
| CN | 103083755 B | 7/2015 |
| EP | 0477551 B1 | 1/1995 |

(Continued)

OTHER PUBLICATIONS

International Search Report and Written Opinion for PCT Application PCT/US2018/028093, dated Aug. 3, 2018, 9 pgs.

(Continued)

*Primary Examiner* — Alfred J Wujciak
(74) *Attorney, Agent, or Firm* — Patterson Thuente Pedersen, P.A.

(57) ABSTRACT

A pole clamp assembly is configured to facilitate removable coupling of one or more medical devices to a support structure. The pole clamp assembly includes a pole clamp that is configured to selectively grip the supporting structure. The pole clamp includes a fastener hub and a locking mechanism. A docking member is configured to operably couple a medical device of the one or more medical devices to the pole clamp. The docking member includes structure defining a fastener hub aperture and one or more recesses into which a portion of the locking mechanism can selectively reside. The locking mechanism is shiftable between a non-engaged position in which the docking member is rotatable relative to the pole clamp, and an engaged position in which rotation of the docking member relative to the pole clamp is inhibited.

13 Claims, 11 Drawing Sheets

(56) References Cited

U.S. PATENT DOCUMENTS

| | | | | |
|---|---|---|---|---|
| 4,905,944 | A | 3/1990 | Jost et al. | |
| 4,921,199 | A | 5/1990 | Villaveces | |
| D314,433 | S | 2/1991 | Frantz | |
| 5,114,023 | A | 5/1992 | Lavin | |
| 5,170,817 | A | 12/1992 | Sunderland | |
| D346,655 | S | 5/1994 | Harris | |
| D379,042 | S | 5/1997 | Meisner et al. | |
| 5,626,320 | A * | 5/1997 | Burrell | B64D 43/00 248/227.4 |
| 5,733,061 | A | 3/1998 | Child | |
| D401,690 | S | 11/1998 | Simm | |
| 5,829,723 | A | 11/1998 | Brunner et al. | |
| D410,846 | S | 7/1999 | Leong et al. | |
| 6,277,109 | B1 | 8/2001 | Harper et al. | |
| 6,290,694 | B1 | 9/2001 | Harper et al. | |
| 6,593,528 | B2 | 7/2003 | Franklin-Lees et al. | |
| D547,863 | S | 7/2007 | Heinsch | |
| 7,556,616 | B2 * | 7/2009 | Fathallah | A61M 5/1413 604/131 |
| D616,250 | S | 5/2010 | Peyton et al. | |
| D628,299 | S | 11/2010 | Held | |
| 7,891,618 | B2 * | 2/2011 | Carnevali | F16M 11/2078 248/228.6 |
| D642,404 | S | 8/2011 | Koehn | |
| 8,011,629 | B2 | 9/2011 | Herkovic | |
| 8,047,482 | B2 | 11/2011 | Poncon et al. | |
| D660,102 | S | 5/2012 | Allred | |
| 8,167,259 | B2 | 5/2012 | Spang, Jr. et al. | |
| 8,256,984 | B2 | 9/2012 | Fathallah et al. | |
| D670,284 | S * | 11/2012 | Choi | D14/253 |
| 8,336,839 | B2 | 12/2012 | Boccoleri et al. | |
| 8,459,602 | B2 | 6/2013 | Herskovic | |
| 8,469,325 | B2 * | 6/2013 | Yu | F16M 13/022 248/316.1 |
| 8,490,937 | B2 * | 7/2013 | Crain | F16M 11/041 248/316.6 |
| D692,132 | S | 10/2013 | Damron | |
| D698,448 | S | 1/2014 | Heck | |
| 8,695,957 | B2 | 4/2014 | Quintania et al. | |
| 8,998,048 | B1 * | 4/2015 | Wu | F16M 13/00 224/420 |
| 9,115,740 | B2 * | 8/2015 | Chang | F16B 2/12 |
| 9,295,778 | B2 | 3/2016 | Kamen et al. | |
| 9,321,168 | B2 | 4/2016 | Brassette | |
| 9,341,308 | B2 | 5/2016 | Lacy | |
| D762,300 | S | 7/2016 | Breitweiser et al. | |
| 9,744,300 | B2 | 8/2017 | Kamen et al. | |
| D799,025 | S | 10/2017 | Johnson et al. | |
| D808,005 | S * | 1/2018 | Peretz | D24/169 |
| D816,864 | S | 5/2018 | Lacy et al. | |
| D828,551 | S | 9/2018 | Zou et al. | |
| D836,205 | S | 12/2018 | Gonzalez et al. | |
| D836,940 | S | 1/2019 | Pena et al. | |
| D846,756 | S | 4/2019 | Lacy et al. | |
| 2002/0134570 | A1 | 9/2002 | Franklin-Lees et al. | |
| 2005/0095063 | A1 | 5/2005 | Fathallah et al. | |
| 2006/0186289 | A1 * | 8/2006 | Hsiung | F16M 11/10 248/200 |
| 2007/0219495 | A1 | 9/2007 | Kato et al. | |
| 2007/0267556 | A1 | 11/2007 | Herskovic | |
| 2008/0203260 | A1 * | 8/2008 | Carnevali | F16M 11/2078 248/316.5 |
| 2010/0065700 | A1 | 3/2010 | Poncon et al. | |
| 2010/0252702 | A1 | 10/2010 | Spang, Jr. et al. | |
| 2010/0258690 | A1 | 10/2010 | Kleitsch et al. | |
| 2010/0314517 | A1 | 12/2010 | Patzer | |
| 2011/0101587 | A1 | 5/2011 | Quintania et al. | |
| 2013/0184676 | A1 | 7/2013 | Kamen et al. | |
| 2013/0324929 | A1 | 12/2013 | Mochizuki et al. | |
| 2014/0046296 | A1 | 2/2014 | Clarke | |
| 2014/0259837 | A1 | 9/2014 | Belliveau et al. | |
| 2014/0294496 | A1 | 10/2014 | Gardiner | |
| 2014/0321096 | A1 | 10/2014 | Kajackas | |
| 2015/0001285 | A1 | 1/2015 | Halbert et al. | |
| 2015/0041419 | A1 | 2/2015 | Hasegawa | |
| 2015/0090849 | A1 | 4/2015 | Breitweiser et al. | |
| 2015/0190567 | A1 | 7/2015 | Asama et al. | |
| 2015/0224252 | A1 | 8/2015 | Borges et al. | |
| 2017/0049956 | A1 | 2/2017 | Kitchen | |
| 2017/0266389 | A1 | 9/2017 | McLoughlin et al. | |
| 2019/0118972 | A1 * | 4/2019 | Yan | F16M 11/2071 |
| 2019/0203879 | A1 * | 7/2019 | Lebedev | A47B 23/02 |
| 2019/0263326 | A1 * | 8/2019 | Yu | F16M 13/02 |

FOREIGN PATENT DOCUMENTS

| | | | |
|---|---|---|---|
| EP | 1233799 | B1 | 2/2006 |
| EP | 3067077 | A1 | 9/2016 |
| JP | 2004305280 | A | 11/2004 |
| JP | D1247382 | | 8/2005 |
| JP | 2007/125248 | A | 5/2007 |
| JP | 4939707 | B2 | 5/2012 |
| JP | D1491891 | | 3/2014 |
| JP | 3200476 | U | 10/2015 |
| RU | 00059734 | | 7/2006 |
| WO | WO 2015/048743 | A2 | 4/2015 |
| WO | WO 2015/108844 | | 7/2015 |

OTHER PUBLICATIONS

Application and file history for U.S. Appl. No. 29/586,206, filed Dec. 1, 2016, inventors Lacy et al., U.S. Pat. No. D846,756.

* cited by examiner

POLE CLAMP ASSEMBLY FOR MEDICAL DEVICES

RELATED APPLICATION INFORMATION

This application claims the benefit of U.S. Provisional Application No. 62/487,189, filed Apr. 19, 2017, the contents of which are fully incorporated herein by reference.

TECHNICAL FIELD

The present disclosure relates generally to a clamp for securing a medical instrument to a pole, and more particularly to such a pole clamp configured to easily engage and disengage a medical device or group of medical devices to a pole.

BACKGROUND

In the hospital or clinical environment, it is often necessary to provide medical devices or instrumentation in proximity to patients, such as near a patient's bedside. For example, during many medical treatments and procedures, patients are provided with intravenous fluid delivery for the infusion of fluids to prevent dehydration, preserve electrolyte balance or deliver other medicaments, such as antibiotics, blood clotting agents, analgesics, and other fluid and/or fluid-like substances. Frequently, intravenous fluid delivery is provided by a programmable infusion pump, such as a controlled gravity drip, peristaltic or syringe pump. Medical devices, such as infusion pumps, are typically attached to a support structure such as an IV pole, bed rail, or other structure by a pole clamp assembly.

Conventional pole clamp assemblies typically include a fixed backstop opposite a contact plate that is connected to a threaded rod having a turn knob at an opposite end. One example of such a pole clamp assembly is depicted in U.S. Published Patent Application No 2015/0198283 assigned to Smiths Medical ASD, Inc., the contents of which are incorporated by reference herein. When securing the pole clamp to the support structure, a caregiver or other user must generally support the medical device with one hand, while turning the knob with the other hand. Removal or repositioning of the medical device likewise requires that the medical device be supported by one hand while unscrewing the knob to free the medical device from the support structure. Depending on the medical treatment or care provided, multiple medical devices may be attached to the support structure in this manner.

While such pole clamp assemblies have been used for many years, they can be awkward and time-consuming to utilize. The ease-of-use and the speed at which a caregiver can secure, remove and/or reposition a medical device is an important consideration. Where multiple medical devices are utilized, the efficient management of space along the support structure to ensure adequate space for the mounting of each medical device is another important consideration. Applicants of the present disclosure have identified a need for a pole clamp assembly to address these concerns.

SUMMARY OF THE DISCLOSURE

Embodiments of the present disclosure provide pole clamp assemblies configured to promote ease-of-use and the speed in which a caregiver or other user can securely mount, remove and/or reposition one or more medical devices in relation to a support structure, while efficiently managing the space along the support structure to ensure adequate space for the mounting of multiple medical devices.

An embodiment of the present disclosure provides a pole clamp assembly configured to facilitate ease in operably coupling one or more medical devices to a supporting structure. The pole clamp assembly can include a pole clamp and a docking member. The pole clamp can be configured to selectively grip the supporting structure. The pole clamp can include a fastener hub and a locking mechanism. The docking member can be configured to operably couple a medical device of the one or more medical devices to the pole clamp. The docking member can include structure defining a fastener hub aperture and one or more recesses into which a portion of the locking mechanism can selectively reside. The locking mechanism can be shiftable between a non-engage position in which the docking member is rotatable relative to the pole clamp, and an engaged position in which rotation of the docking member relative to the pole clamp is inhibited.

In an embodiment, the locking mechanism includes a lock body pivotable about a first end between the engaged position and the non-engaged position. In an embodiment, the locking mechanism is biased towards the engaged position. In an embodiment, the docking member includes a docking member body configured to operably couple a medical device, and a hub portion configured to operably couple to the pole clamp. In an embodiment, the docking member includes a projection configured to be at least partially inserted into a retaining feature of the medical device. In an embodiment, the projection comprises a first end surface, a bottom surface, a pair of side surfaces, and a top surface. In an embodiment, the projection further includes one or more tabs operably coupled to one or more of the pair of side surfaces. In an embodiment, the structural support for the projection is in part provided by a keel member extending between the structure defining the bottom surface and the top surface. In an embodiment, the projection consists of a pair of side surfaces. In an embodiment, structural support for the projection is in part provided by a lateral rib extending between the pair of side surfaces. In an embodiment, the hub portion further includes a hub face defining the fastener hub aperture and the one or more recesses. In an embodiment, the hub face to find a plurality of recesses circumferentially arranged around the hub fastener aperture. In an embodiment, a longitudinal axis of the docking member body is substantially orthogonal to the hub face. In an embodiment, a longitudinal axis of the docking member body is positioned at an obtuse angle relative to the hub face.

The summary above is not intended to describe each illustrated embodiment or every implementation of the present disclosure. The figures and the detailed description that follow more particularly exemplify these embodiments.

BRIEF DESCRIPTION OF THE DRAWINGS

The disclosure can be more completely understood in consideration of the following detailed description of various embodiments of the disclosure, in connection with the accompanying drawings, in which.

Figure 1A:
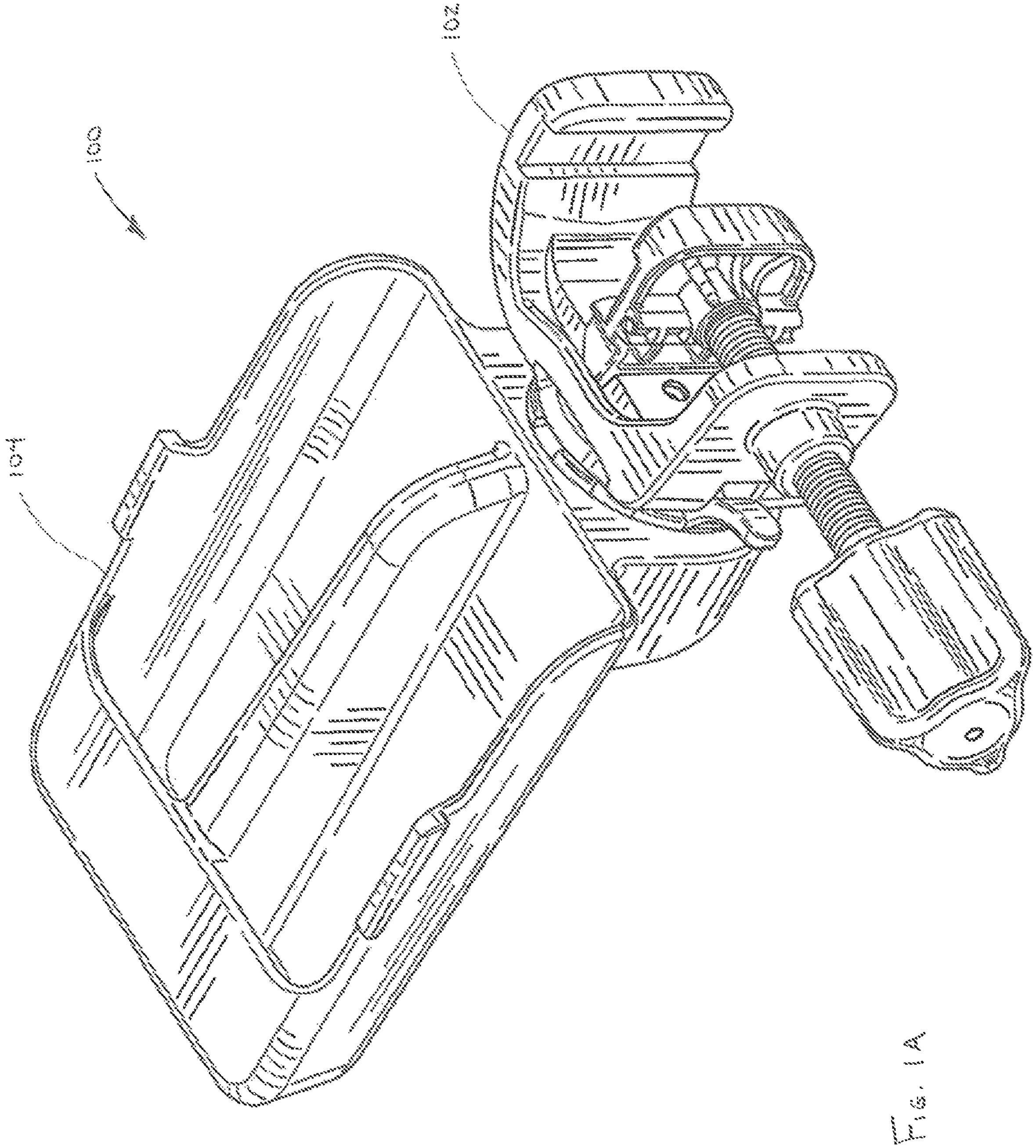
FIG. 1A is a perspective view depicting a pole clamp assembly, in accordance with an embodiment of the disclosure.

While embodiments of the disclosure are amenable to various modifications and alternative forms, specifics thereof shown by way of example in the drawings will be described in detail. It should be understood, however, that the intention is not to limit the disclosure to the particular embodiments described. On the contrary, the intention is to cover all modifications, equivalents, and alternatives falling within the spirit and scope of the subject matter as defined by the claims.

DETAILED DESCRIPTION

Figure 1B:
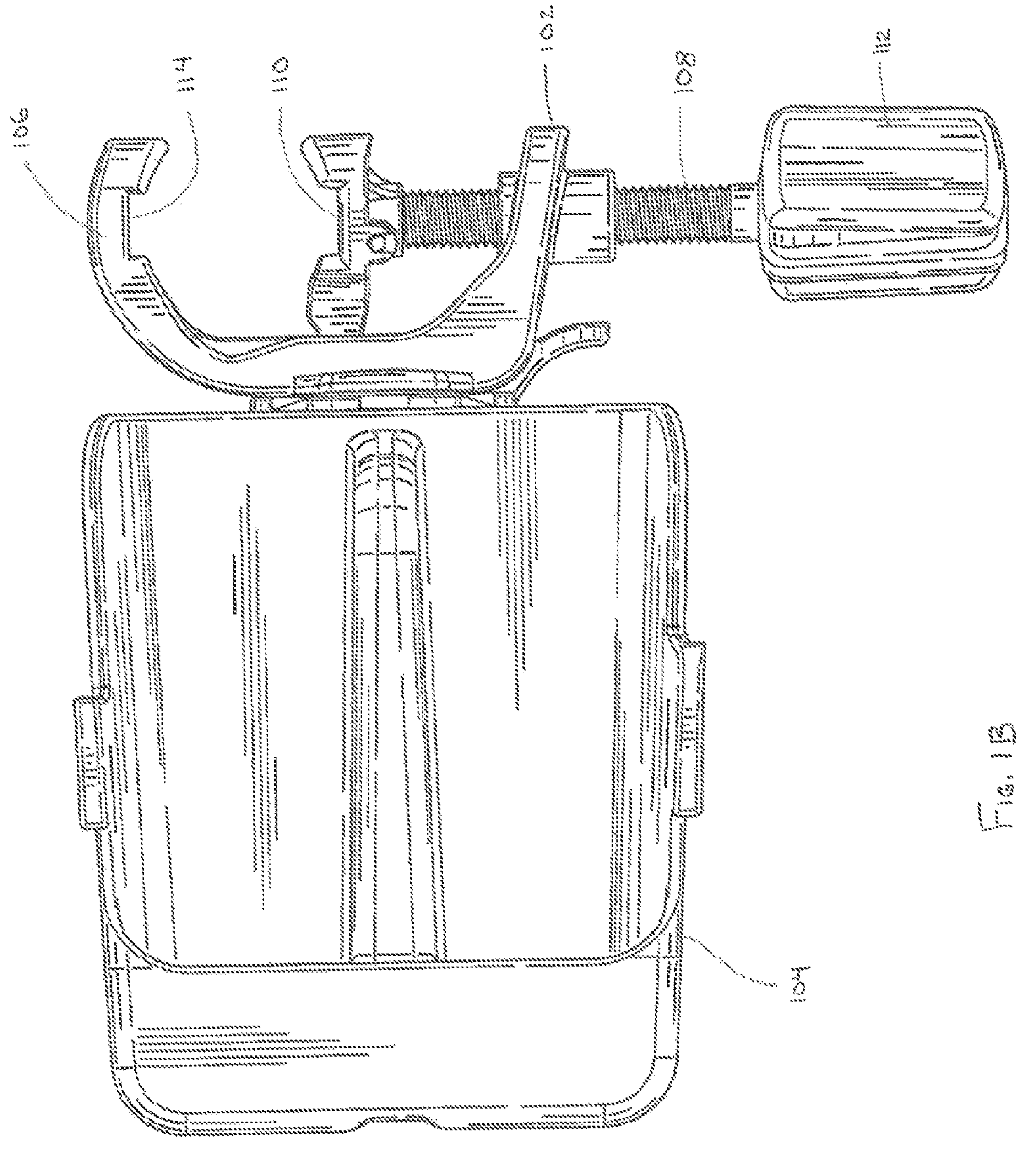
FIG. 1B is a plan view depicting the pole clamp assembly of FIG. 1A.

Referring to FIGS. 1A-B, a pole clamp assembly 100 is depicted in accordance with an embodiment of the disclosure. In an embodiment, the pole clamp assembly 100 can include a pole clamp 102 and a docking member 104. As described in further detail below, the pole clamp 102 can be configured to be clamped onto an IV pole or other supporting structure. The docking member 104 can be configured to be operably coupled to the pole clamp 102. In an embodiment, the docking member 104 can further be selectively rotated relative to the pole clamp 102, so as to operably couple the docking member 104 at a desired angle relative to the pole clamp 102. A first medical device, such as an infusion pump, can be selectively coupled to the docking member 104. For example, in an embodiment, a portion of the docking member 104 can be configured to slide into a corresponding recess defined in the medical device. One or more additional medical devices can be operably coupled to the first medical device in a stacked configuration. Accordingly, the pole clamp assembly 100 is configured to enable rapid connection and disconnection of one or more medical devices from an IV pole or other supporting structure in a space efficient manner.

Figure 2:
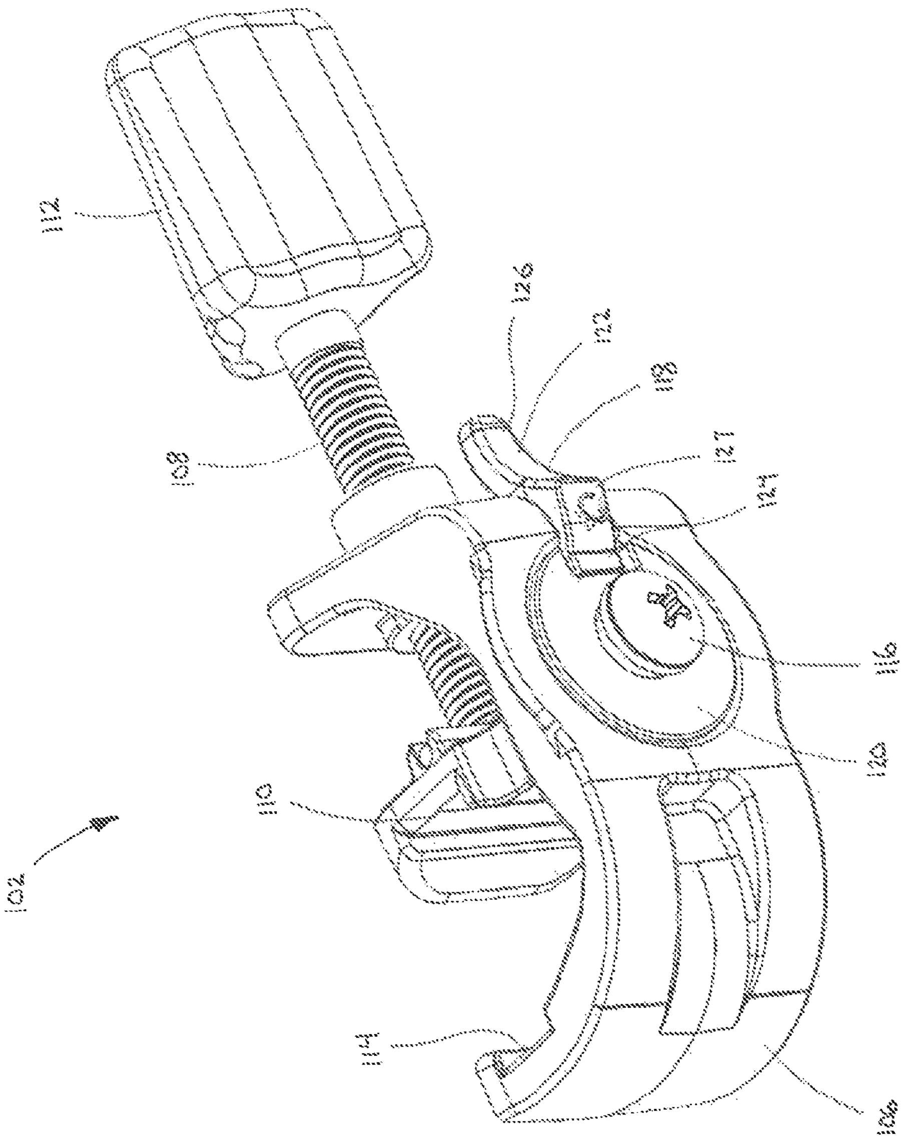
FIG. 2 is a perspective view depicting a pole clamp, in accordance with an embodiment of the disclosure.

Referring to FIG. 2, a pole clamp 102 is depicted in accordance with an embodiment of the disclosure. In an embodiment, the pole clamp 102 can include a pole clamp body 106, threaded adjustment rod 108, contact plate 110, and rotational knob 112. In an embodiment, the pole clamp 102 can be secured to an IV pole or other supporting structure by a caregiver or other user manually rotating the rotational knob 112, thereby causing the threaded adjustment rod 108 to advance the contact plate 110 towards an opposing face 114 of the pole clamp body 106, so as to grip the IV pole or supporting structure between the contact plate 110 and the opposing face 114. FIG. 1B depicts a plan view of a pole clamp assembly 102 operably coupled to the docking member 104. Notably, in an embodiment, the contact plate 110 does not rotate with the rotation of the threaded adjustment rod 108 and rotational knob 112. Rather, motion of the contact plate 110 is restricted to axial movement toward and away from the opposing face 114 as the threaded adjustment rod 108 is advanced and retracted.

With continued reference to FIG. 2, the pole clamp 102 can further include a fastener hub 116 and a locking mechanism 118. The fastener hub 116 can be configured as the primary coupling mechanism to facilitate coupling between the pole clamp 102 and the docking member 104. In an embodiment, the fastener hub 116 can be operably coupled to the pole clamp body 106. For example, in an embodiment, the fastener hub 116 can be threadably coupled with a corresponding threaded aperture defined through at least a portion of the pole clamp body 106. As depicted in FIG. 2, the fastener hub 116 is configured as a pan bolt head having a slightly rounded head with short vertical sides atop a narrower diameter shaft. Other fastener hub configurations configured to serve as a coupling mechanism between the pole clamp 102 and the docking member 104 are also contemplated. To improve the connection between the pole clamp 102 and the docking member 104, in some embodiments, the fastener hub 116 can be positioned within a recess 120 defined within the pole clamp body 106. For example, in an embodiment, the fastener hub 116 can be substantially centered within a generally circularly shaped recess 120.

The locking mechanism 118 can be configured to provide a secondary coupling mechanism to facilitate coupling between the pole clamp 102 and the docking member 104. In an embodiment, the locking mechanism 118 is pivotable between an engaged position (as depicted in FIG. 2) and a non-engaged position. For example, in an embodiment, the locking mechanism 118 can include a lock body 122 pivotably coupled to the pole clamp body 106 proximal to the first end 124 of the lock body 122. A biasing mechanism (not depicted) positioned between the pole clamp body 106 and the lock body 122 can bias the locking mechanism 118 to the engaged position. Applying an external force proximal to a second end 126 of the lock body 122, for example by the finger of a caregiver or user, can cause the lock body 122 to pivot about its first end 124, thereby shifting the locking mechanism 118 to the non-engaged position.

Referring to FIGS. 3A-D, a docking member 104 is depicted in accordance with an embodiment of the disclosure. The docking member 104 can be fabricated of a substantially rigid material, such as plastic, fiberglass, metal, or a composite thereof. In some embodiments, the docking member 104 is a unitary member. In other embodiments, the docking member 104 is assembled from a plurality of components. The docking member 104 can generally include a docking member body 128 and a hub portion 130.

The hub portion 130 can be configured to operably couple to the pole clamp 102. In an embodiment, the hub portion 130 can be formed as an extension of the docking member body 128. For example, in the normal gravitational frame of reference with the docking member 104 in the orientation depicted in FIGS. 3A-B, the hub portion 130 can generally extend downward from a bottom surface 132 of the docking member body 128.

The hub portion 130 can define a hub face 134 on one or more surfaces thereof. In an embodiment, the hub face 134 can have a generally circular shape, although other hub face configurations are also contemplated. The hub face 134 can define a fastener hub aperture 136 shaped and sized to at least receive at least a portion of the fastener hub 116 of the pole clamp 102 therein, thereby facilitating an operable coupling between the pole clamp 102 and the docking member 104. In an embodiment, the fastener hub aperture 136 can be substantially circular in shape, and can be positioned in the approximate center of the hub face 134. Other fastener hub aperture shapes and positions are also contemplated.

Figure 3A:
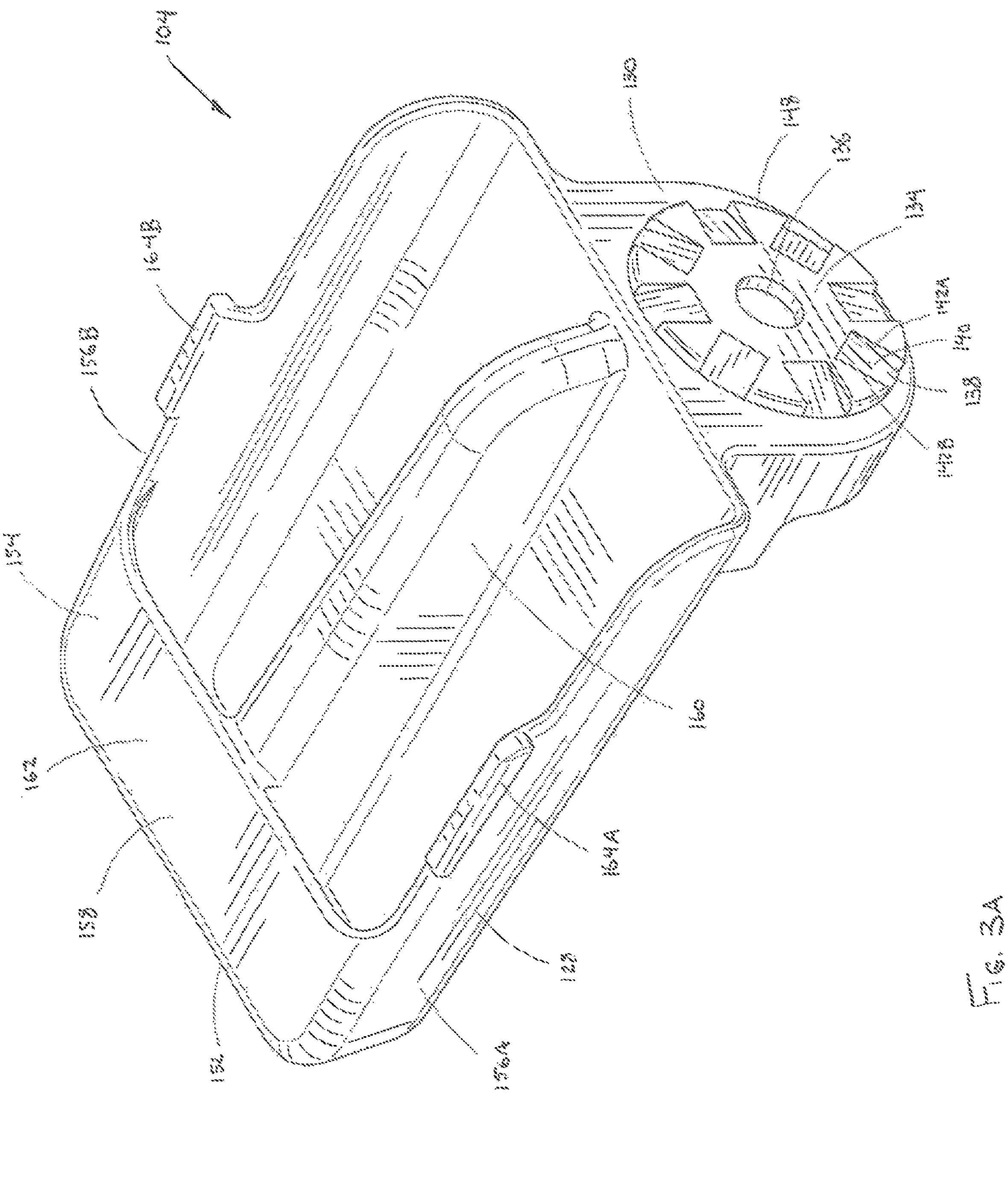
FIG. 3A is a rear perspective view depicting a docking member in accordance with a first embodiment of the disclosure.

In an embodiment, the hub face 134 can further define one or more recesses 138 shaped and sized to correspondingly mate with a portion 127 of the locking mechanism 118 of the pole clamp 102. Each of the one or more recesses 138 can include a base portion 140 and one or more sidewalls 142A/B. In an embodiment, the base portion 140 can form an angle of between 0-10° with respect to the surface of the hub face 134. In another embodiment, the base portion 140 can form an angle of between 10-20° with respect to the surface of the hub face 134. In an embodiment, the one or more recesses 138 can be oriented along a periphery of the hub face, with an axis of each recess 138 projecting radially toward a center of the hub face 134. For example, as depicted in FIG. 3C, in an embodiment, the hub face 134 can include eight recesses 134, wherein the axis of each recess 138 extends radially outward from a center of the hub face 134 with an angle θ between adjacent axes. In an embodiment, the angle θ can approximate 45° between adjacent axes. Other quantities and configurations of recesses are also contemplated.

Figure 3B:
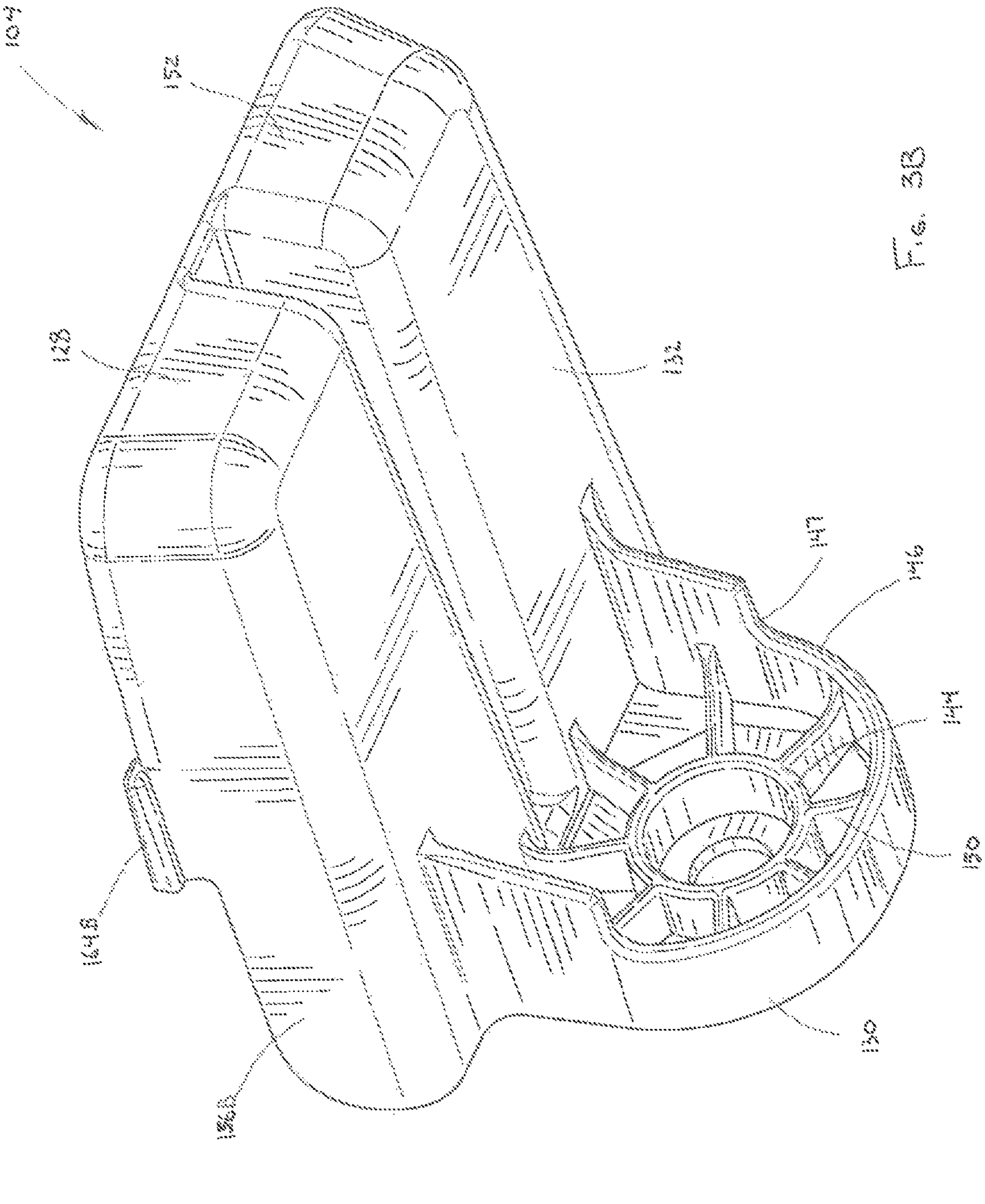
FIG. 3B is a front perspective view depicting the docking member of FIG. 3A.
Figure 3C:
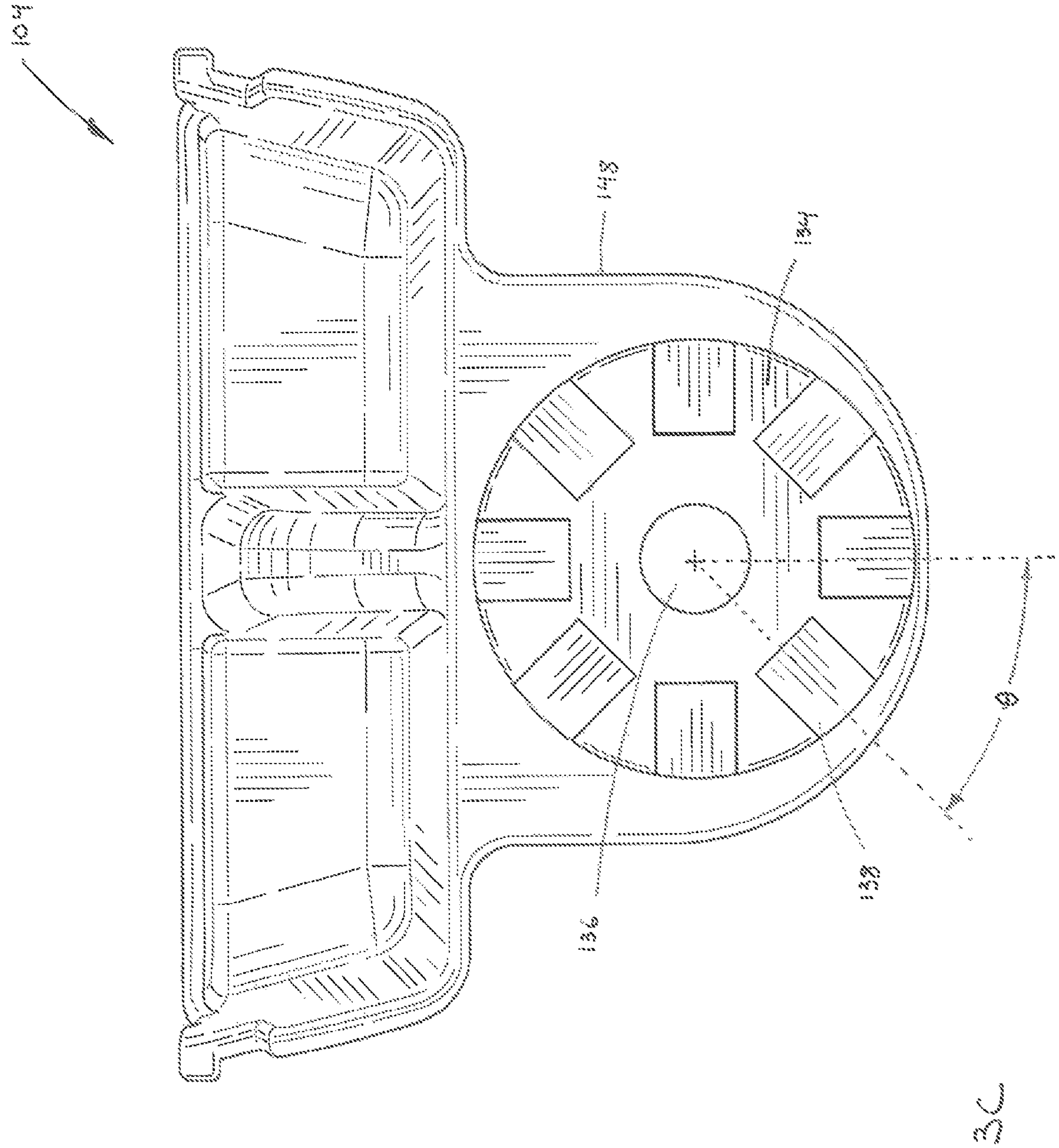
FIG. 3C is a rear view depicting the docking member of FIG. 3A.

As depicted in FIG. 3B, the hub face 134 of the hub portion 130 can be supported by a an arrangement of structural supports configured to provide strength and rigidity of the docking member 104, while minimizing the overall weight and the material used in the production of the docking member 104. For example, in an embodiment, the hub portion 130 can include a fastener hub aperture rim 144 at least partially surrounding the fastener hub aperture 136, opposite to the hub face 134 depicted in FIG. 3A. An outer rim 146 depicted in FIG. 3B can be provided in proximity to an outer edge 148 of the hub portion 130, opposite to the hub face 134. In an embodiment, the outer rim 146 can be operably coupled to a portion of the docking member body 128 to provide additional rigidity and support. One or more ribs 150 can extend between the fastener hub aperture rim 144 and the outer rim 146 and/or a portion of the docking member body 128. In an embodiment, the hub portion 130 can include eight ribs 150 configured to extend radially outward from the fastener hub aperture rim 144. Other configurations of structural supports are also contemplated.

With continued reference to FIGS. 3A and 3B, the docking member body 128 can be configured to at least partially extend into a retaining feature of a medical device, thereby enabling the medical device to be selectively coupled to the docking member 104. In an embodiment, the docking member body 128 can include a first (distal) end 152, bottom surface 132, top surface 162, and opposing side portions 156A/B. The hub portion 130 can be operably coupled to the docking member 128 opposite the first end 152. In an embodiment, the first end 152, and a portion of the top surface 162, bottom surface 132 and side portions 156A/B can generally form a projection 158 configured to be at least partially inserted into a corresponding retaining feature of a medical device. In some embodiments, a supporting keel member 160, positioned between the side portions 156A/B, can extend between the bottom surface 132 and the top surface 162. The top surface 162 can operably couple the side portions 156A/B, keel member 160 and first end 152 to add rigidity and structural support to the projection 158. One or more tabs 164 (in the example of FIG. 3A, tabs 164A/B) can extend from the side portions 156A/B and/or top surface 162 to engage with a corresponding latch of the supporting channel of the medical device, as an aid in securing the medical device to the docking member 104.

Figure 3D:
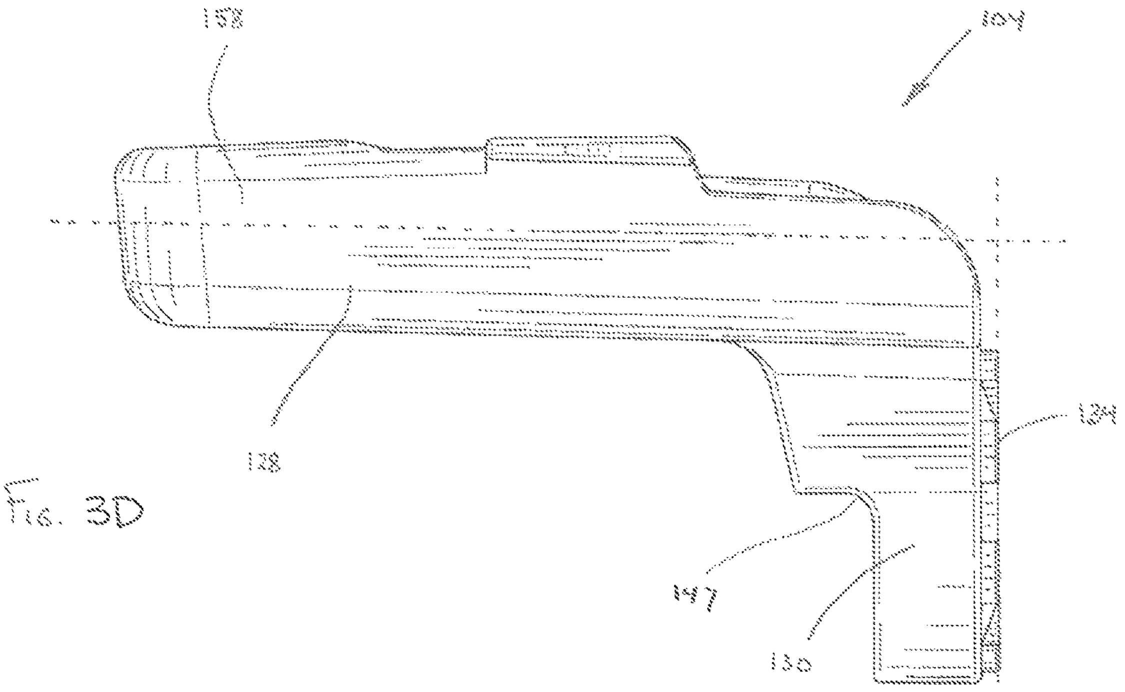
FIG. 3D is a profile view depicting the docking member of FIG. 3A.

As depicted in FIG. 3D, a longitudinal axis of the projection 158 can extend substantially orthogonally to the hub face 134, such that a medical device selectively coupled to the docking member 104 extends in a substantially horizontal plane when attached to a substantially vertical IV pole or other supporting structure.

Figure 7B:
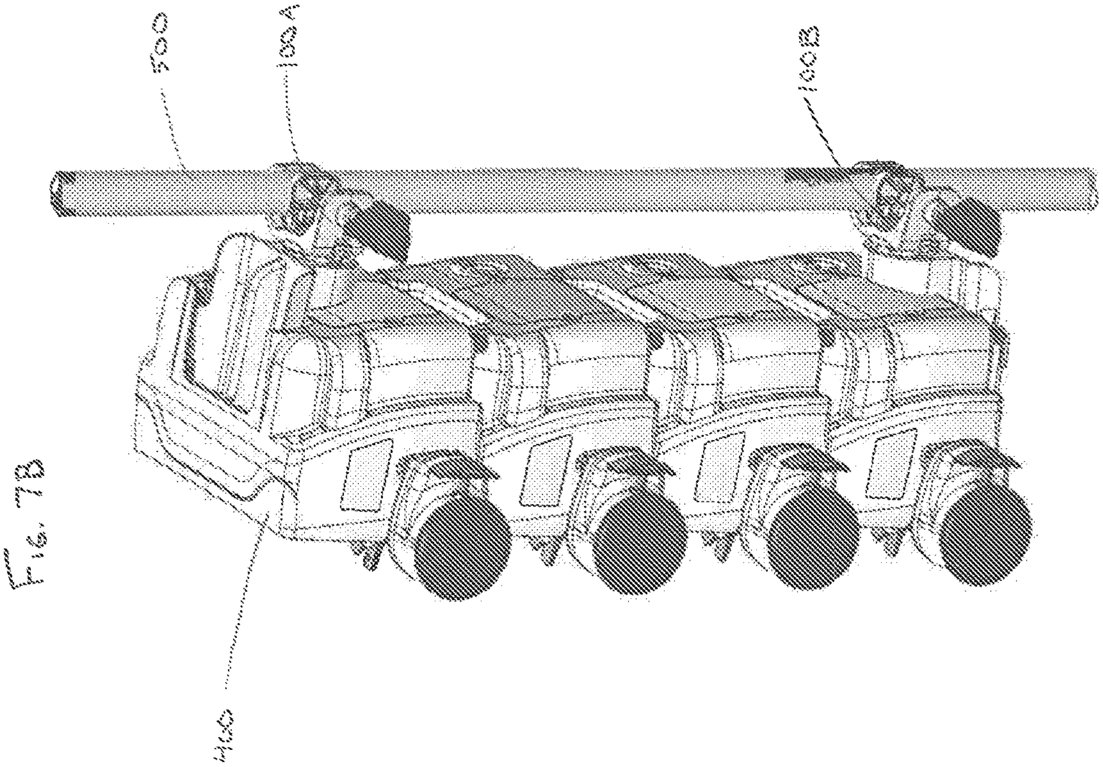
FIG. 7B is a close-up view depicting the operable coupling between the medical device and support structure depicted in FIG. 7A.
Figure 7A:
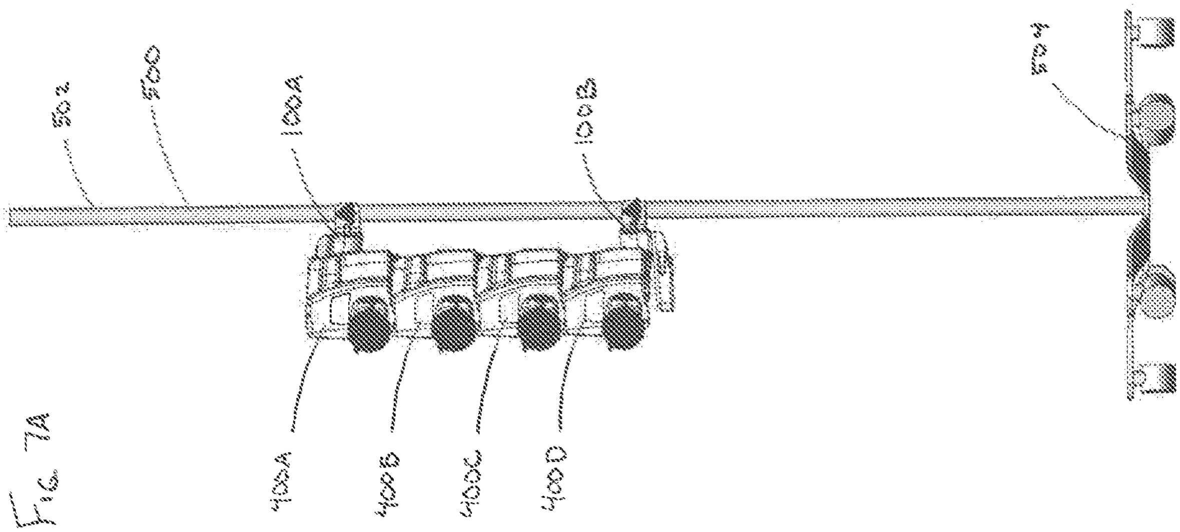
FIG. 7A depicts the operable coupling of a medical device to a support structure via a pole clamp assembly, in accordance with an embodiment of the disclosure.

Alternatively, the docking member 104 can be inverted when mounted to an IV pole or other supporting structure, for the purpose of supporting the bottom of a medical device and/or stack of medical devices (as depicted in FIGS. 7A and 7B). With additional reference to FIG. 3B, in an embodiment, at least a portion of the outer rim 146 of the hub portion 130 can be contoured to conform to a bottom portion of a medical device when the docking member 104 is inverted. For example, in an embodiment, the outer rim 146 can define a cut out or set-back portion 147 configured to conform to and/or support a corresponding portion of a medical device positioned above the inverted docking member 104.

Figure 4:
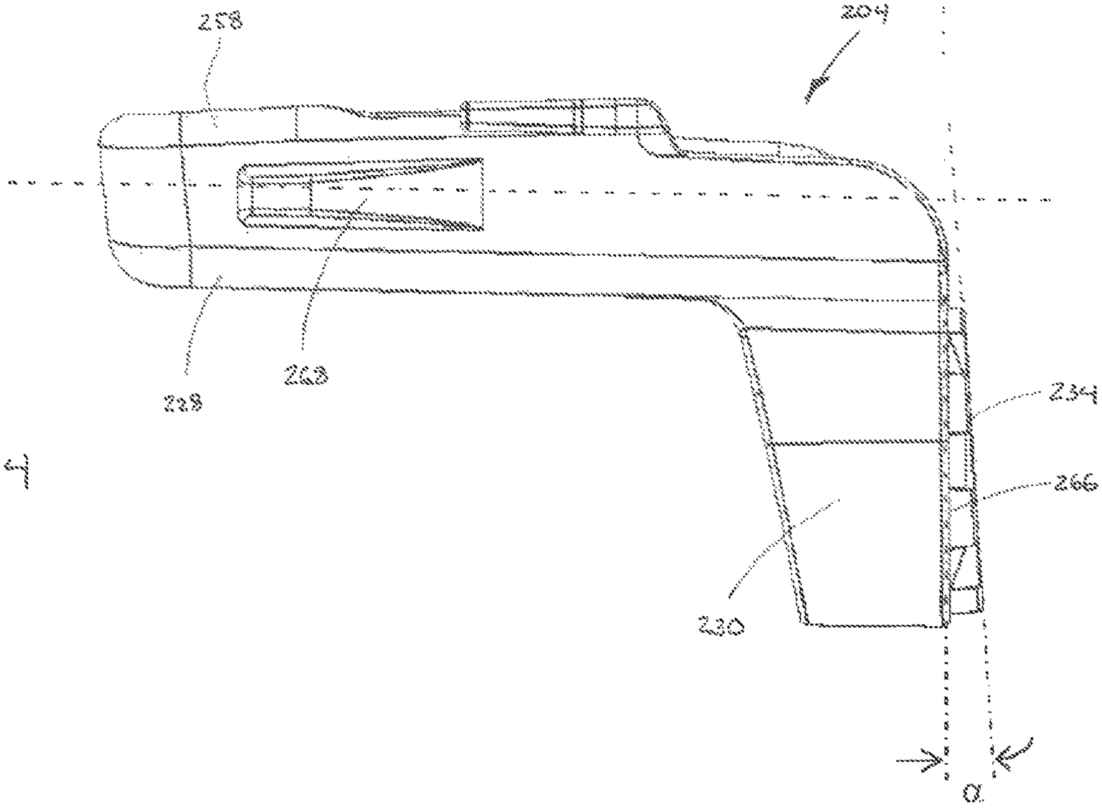
FIG. 4 is a profile view depicting a docking member in accordance with a second embodiment of the disclosure.

Referring to FIG. 4, a second embodiment of a docking member, 204, is depicted in accordance with the disclosure. In this embodiment, a longitudinal axis of the projection 258 can extend at an oblique angle relative to the hub face 234, such that a medical device selectively coupled to the docking number 204 would thereby be tilted slightly upward from a horizontal plane when attached to a substantially vertical IV pole or other supporting structure. In an embodiment, this can be accomplished by orienting the hub face 234 at an angle α with respect to an exterior surface 266 of the hub portion 230. As depicted in the example of FIG. 4, the angle α can be approximately 3°. In other embodiments, the angle α can be between 0-10°. Other angular configurations are also contemplated.

The docking member 204 can further include one or more channels or indents 268, which can be positioned on the respective sides of the docking member body 228. In some embodiments, the one or more indents 268 can further aid in operably coupling the projection 258 with the corresponding retaining feature of a medical device. Other features of the docking member 204 can be similar to previously disclosed embodiments.

Figure 5A:
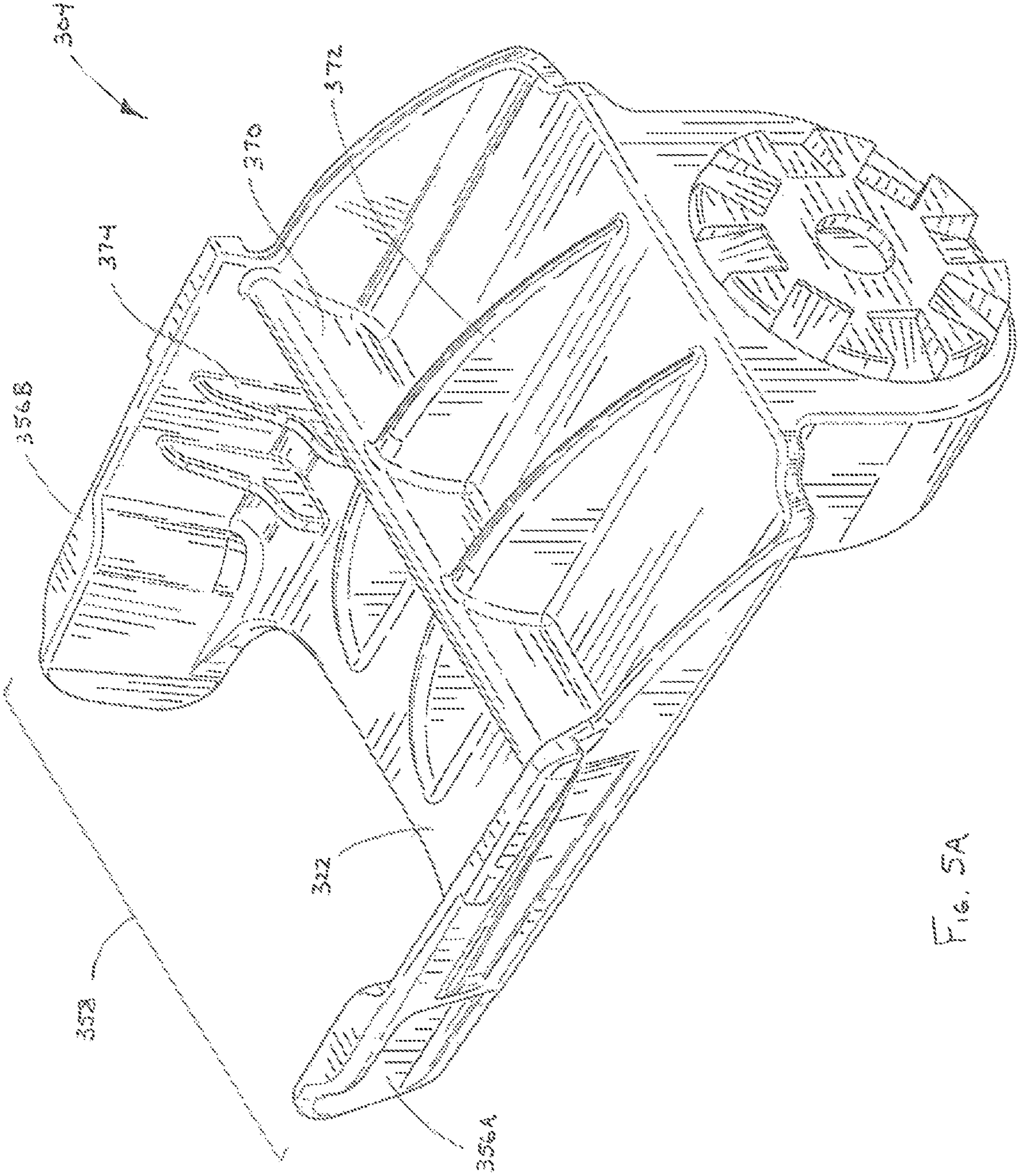
FIG. 5A is a rear perspective view depicting a docking member in accordance with a third embodiment of the disclosure.
Figure 5B:
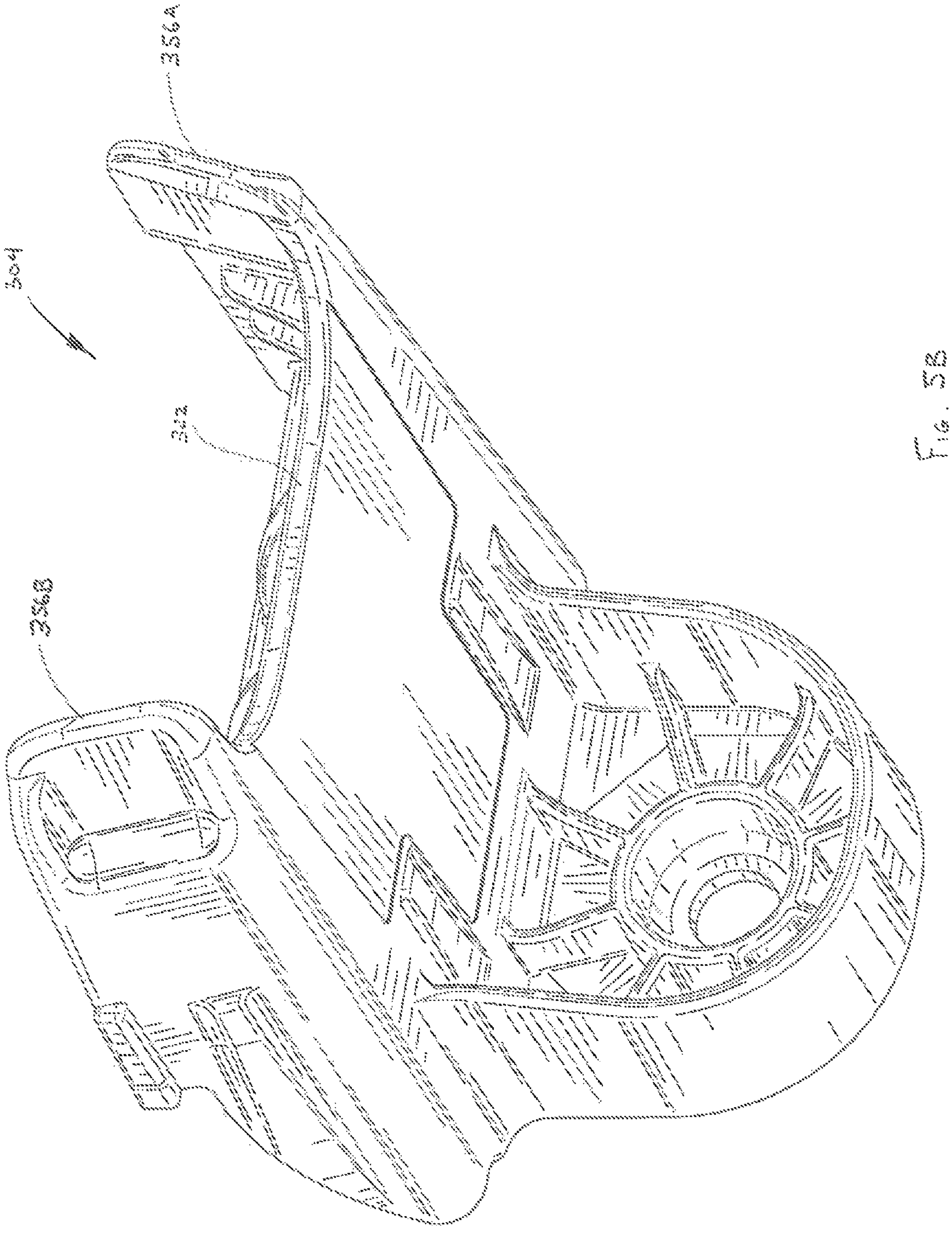
FIG. 5B is a front perspective view depicting the docking member of FIG. 5A.

Referring to FIGS. 5A-B, a third embodiment of a docking member 304 is depicted in accordance with the disclosure. In this embodiment, the projection 358 is primarily present in or limited to side portions 356A/B, and optionally a portion of the bottom surface 332, but lacking a top surface (as is present in previous embodiments). The distal end (away from the hub portion) of projection 358 is thus configured to be open, as depicted in FIGS. 5A and 5B. In some embodiments, omission of a top surface on projection 358 aids in the insertion and withdrawal of the projection 358 into and out of a corresponding retaining feature of a medical device. In particular, where the retaining feature of a medical device includes a handle for gripping the medical device, a projection 358 that is primarily limited to side portions 356A/B and a bottom surface 332 enables gripping of the handle of the medical device with limited or no interference from the projection 358.

In place of a keel member and top surface, rigidity and support of the projection 358 can be provided by a lateral rib 370 extending between the side portions 356A/B, so as to operably couple the side portions 356A/B to the bottom surface 332. One or more additional supporting ribs 372 can extend substantially orthogonally to the lateral rib 370, so as to further operably couple the lateral rib 370 to the bottom surface 332. In an embodiment, the additional supporting ribs 372 can extend from both sides of the lateral rib 370. Additional material and additional ribs 374 can be included in the side portions 356A/B to further add to the rigidity and support of the projection 358. For example, as depicted in FIG. 5A, the docking member 304 can include one or more additional ribs 374, so as to further operably couple the side portions 356A/B to the bottom surface 332. Other configurations of structural supports are also contemplated. Other features of the docking member 304 can be similar to previously disclosed embodiments. Docking member 304 may include a hub face oriented at an angle with respect to an exterior surface of the hub portion, as described with respect to other embodiments.

Figure 6A:
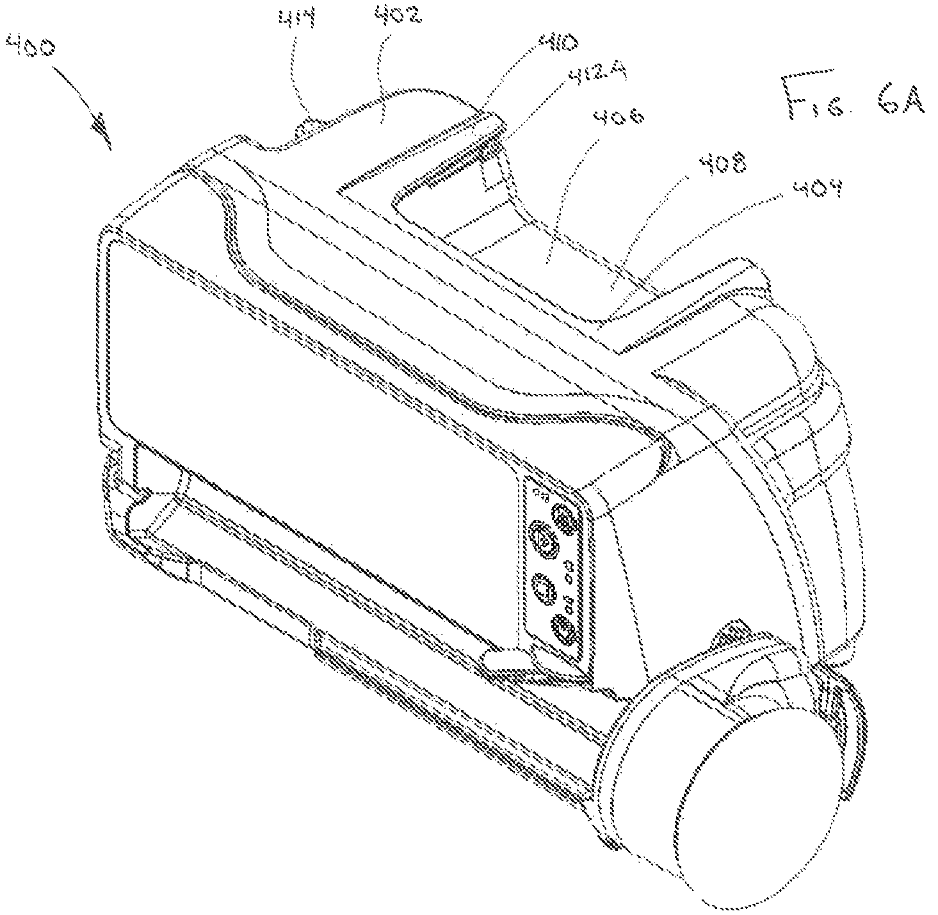
FIG. 6A is a front perspective view of a medical device in accordance with an embodiment of the disclosure.
Figure 6B:
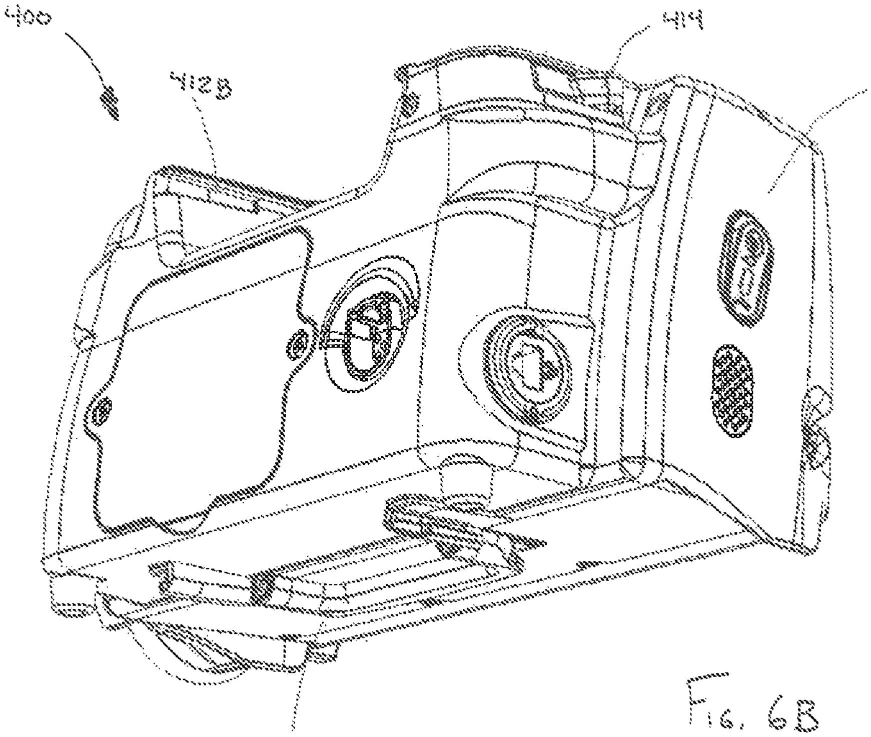
FIG. 6B is a rear perspective view depicting the medical device of FIG. 6A.

In operation, the pole clamp assemblies, as described by example or otherwise contemplated herein, can be configured to operably couple a medical device to an IV pole or other supporting structure. FIGS. 6A-B depict an example of a medical device 400, in the form of a syringe pump, for use with a pole clamp assembly such as, for example, assembly 100. As depicted, a housing 402 of the medical device can generally define a handle 404. The handle 404 can be integrally molded into an outer surface of the housing 402, and be partially defined by a central recess 406 defined within the housing 402, and can provide a convenient structure for grasping, manipulating, and moving the medical device 400.

In some embodiments, the handle 404 can be part of a retaining feature 408, configured to provide releasable locking engagement with the pole clamp assembly 100 and other medical devices. The retaining feature 408 can include an upper lip portion 410 that extends inwardly around the central recess 408. In some embodiments, the upper lip portion 410 can extend around three sides of the central recess 406 to form a general "U" shape when viewed from above. In some embodiments, a section of the upper lip portion 410 in a middle portion of the retaining feature 408 can comprise the handle 404. A recessed space in which a caregiver or user can place his or her fingers in order to readily grasp the handle 404 can be defined beneath the handle 404 of the upper lip portion 410.

The retaining feature 408 can further include one or more receiving grooves 412, which can be defined underneath the upper lip portion 410. In some embodiments, the retaining feature 408 includes a pair of receiving grooves 412A/B provided on opposite sides of the retaining feature 408. In an embodiment, the receiving grooves 412A/B can be configured as slots that progressively narrow in structure and converge inwardly from a rearward face of the housing 402.

The retaining feature 408 can further include a latch assembly 414 configured to selectively lock the medical device 400 to the pole clamp assembly 100 and/or other medical devices. The latch assembly 414 can be positioned on one side of the retaining feature 408 proximal to one of the receiving grooves 412. In an embodiment, the latch assembly 414 can be manipulated between an engaged position and a disengaged position. The latch assembly 414 can be biased to the engaged position. In an embodiment, the latch assembly can further be configured to produce an audible noise, such as a "click" sound, to provide auditory confirmation of engagement with the pole clamp assembly 100.

As depicted in FIG. 6B, the housing 402 can further include a downwardly extending projection 416 on a bottom portion of the medical device 400. In an embodiment, the extending projection 416 can be shaped and sized to be received within corresponding grooves (similar to receiving grooves 412) of another medical device, thereby enabling the medical device 400 to be readily stacked with other medical devices having a similar retaining feature.

Referring to FIGS. 7A-B, the utilization of a pair of docking members 100A/B to operably couple or removably secure a stack of, for example, four medical devices 400A-D to an IV pole 500 is depicted in accordance with an embodiment of the disclosure. Other configurations of coupling one or more medical devices 400 to an IV pole 500 or other supporting structure are also contemplated. For example, in some embodiments, a single docking member 100 can be utilized to couple one or more medical devices 400 to the IV pole 500. In other embodiments, depending upon the weight of the medical devices and the required support, three or more docking members 100 can be utilized to operably couple a stack of medical devices to the IV pole 500.

In an embodiment, the IV pole 500 can include a vertical support structure 502 supported by a wide wheelbase 504 to inhibit the IV pole 500 from tipping. The IV pole 500, in some embodiments, can further be provided with an AC power supply and/or consolidated Ethernet connection. Accordingly, the IV pole 500, in combination with one or more pole clamp assemblies 100, enables the individual installation and removal of medical devices, thereby enabling customized patient-specific infusion pump configurations.

The selective coupling of one or more medical devices 400 to an IV pole 500 or other support structure generally includes operably coupling one or more pole clamp assemblies 100 to the IV pole 500 and one or more medical devices 400 to the one or more pole clamp assemblies 100, although it should be understood that these steps may be performed in the opposite order and/or simultaneously. For example, in removably coupling a pole clamp assembly 100 to an IV pole 500, a caregiver or user positions the pole clamp assembly 100 relative to the IV pole 500 such that the IV pole 500 passes through a space defined between the contact plate 100 and the opposing face 114 of the pole clamp body 106. In some cases, this may require rotation of the rotational knob 112 (e.g., counterclockwise rotation), so as to shift the contact plate 110 laterally apart from the opposing face 114, thereby enabling the IV pole 500 to be positioned therebetween. The pole clamp 102 can be secured to the IV pole 500 by opposite rotation of the rotational knob 112 (e.g., clockwise rotation) so as to shift the contact plate 110 laterally toward the opposing face 114 until a force sufficient to inhibit movement of the pole clamp 102 relative to the IV pole 500 is established.

The docking member 104 can be operably coupled to the pole clamp 102 via fastener hub 116 and fastener hub aperture 136. For example, in an embodiment, a first portion of the fastener hub 116 can traverse through the fastener hub aperture 136 and threadably couple to pole clamp body 106, while a second portion of the fastener hub 116, having an outer dimension larger than the fastener hub aperture 136, can effectively secure the docking member 104 to the pole clamp 102. In this manner, the fastener hub 116 and fastener hub aperture 136 serve as the primary coupling mechanism to facilitate a coupling between the pole clamp 102 and the docking member 104.

A secondary coupling mechanism to facilitate a coupling between the pole clamp 102 and the docking member 104 can be provided by an interaction between the locking mechanism 118 of the pole clamp 102 and the one or more recesses 138 defined in the hub face 134 of the docking member 104. Applying an external force proximal to a second end 126 of the lock body 122 of the locking mechanism 118 can cause the lock body 122 to pivot about a first end 124, thereby shifting the locking mechanism 118 to a non-engaged position. In the non-engaged position, the docking member 104 is free to rotate about the fastener hub 116 of the pole clamp 102. Accordingly, simultaneously applying an external force to the locking mechanism 118, while rotating the docking member 104 relative to the pole clamp 102, enables a caregiver to adjust the angle between the docking member 104 and the pole clamp 102, and thereby the angle and/or orientation of the medical device coupled thereto as desired.

In some embodiments, the locking mechanism 118 can be naturally biased to an engaged position, such that release of the external force causes the lock body 122 to pivot about its first end 124 in the opposite direction, thereby shifting the locking mechanism 118 into engaging contact with the hub face 134 of the docking member 104. In particular, in the engaged position, a portion of the lock body 122 of the locking mechanism 118 can enter a recess 138 of the one or more recesses defined within the hub face 134, thereby inhibiting the docking member 104 from rotation relative to the pole clamp 102 when the locking mechanism 118 resides in a recess 138.

A first medical device 400A can be operably coupled to a docking member of a pole clamp assembly 100A by insertion of the projection 158 of the docking member into the corresponding retaining feature 408 (as illustrated in FIG. 6A) of the medical device 400A. In some embodiments, the one or more tabs 164A/B defined by the docking member body 128 can be configured to slide along receiving grooves 412A/B of the retaining feature 408. A latch assembly 414, closely associated with at least one of the receiving grooves 412A, can inhibit the tab 164B of the docking member received within the receiving groove 412A of the retaining feature 408 from backing out, once inserted. In this manner, the latch assembly 414 can inhibit release of the medical device 400A from the docking member once operably coupled. In some embodiments, the latch assembly 414 can further provide an audible and/or tactile "click" as confirmation that the medical device 400A has been properly coupled to the docking member of the pole clamp assembly 100A.

Additional medical devices 400B-D can be operably coupled to the first medical device 400A by insertion of the extending portion 416 the first medical device 400A into the corresponding retaining feature 408 of a second medical device 400B, thereby enabling the medical devices 400A-B to be operably coupled together. Additional medical devices 400 can be operably coupled in the same manner.

Additional pole clamp assemblies 100 can be utilized to couple various medical devices of a stack of medical devices 400 to the IV pole 500. For example, as depicted in FIGS. 7A-B, a first pole clamp assembly 100A can be utilized at the top of the stack of medical devices 400A-D, and a second pole clamp assembly 100B can be utilized at the bottom of the stack of medical devices 400A-D, such that the first and second pole clamp assemblies 100A/B share in supporting the weight of the stack of medical devices 400A-D. In an embodiment, the second pole clamp assembly 100B can be inverted relative to the orientation of the first pole clamp assembly 100A. In an embodiment, the pole clamp assembly 100B can operably couple to the extending projection 416 of the bottom medical device 400D. In other embodiments, the second pole clamp assembly 100B, and other subsequent pole clamp assemblies, can be inserted into the retaining features 408 of the various medical devices of a stack of medical devices.

It should be understood that the individual steps used in the methods of the present teachings may be performed in any order and/or simultaneously, as long as the teachings remain operable. Furthermore, it should be understood that the apparatus and methods of the present teachings can include any number, or all, of the described embodiments, as long as the teachings remain operable.

Various embodiments of systems, devices, and methods have been described herein. These embodiments are given only by way of example and are not intended to limit the scope of the claimed subject matter. It should be appreciated, moreover, that the various features of the embodiments that have been described may be combined in various ways to produce numerous additional embodiments. Moreover, while various materials, dimensions, shapes, configurations and locations, etc. have been described for use with disclosed embodiments, others besides those disclosed may be utilized without exceeding the scope of the claimed subject matter.

Persons of ordinary skill in the relevant arts will recognize that the subject matter hereof may comprise fewer features than illustrated in any individual embodiment described above. Reference in the specification to "an embodiment," "an embodiment," or "some embodiments" means that a particular feature, structure, or characteristic, described in connection with the embodiment, is included in at least an embodiment of the disclosure. Appearances of the phrases "in one embodiment" and "in an embodiment" in various places in the specification are not necessarily all referring to the same embodiment. Moreover, the embodiments described herein are not meant to be an exhaustive presentation of the ways in which the various features of the subject matter hereof may be combined, nor are the embodiments mutually exclusive combinations of features. Rather, the various embodiments can comprise a combination of different individual features selected from different individual embodiments, such that, as understood by persons of ordinary skill in the art, elements described with respect to an embodiment can be implemented in other embodiments even when not described in such embodiments unless (i) contrary to the systems, devices, and methods described by example or otherwise contemplated herein, or (ii) any part of the disclosure would be rendered inoperable, or (iii) otherwise noted.

Although a dependent claim may refer in the claims to a specific combination with one or more other claims, other embodiments can also include a combination of the dependent claim with the subject matter of each other dependent claim or a combination of one or more features with other dependent or independent claims. Such combinations are proposed herein unless it is stated that a specific combination is not intended. Furthermore, it is intended also to include features of a claim in any other independent claim even if this claim is not directly made dependent to the independent claim.

Any incorporation by reference of documents above is limited such that no subject matter is incorporated that is contrary to the explicit disclosure herein. Any incorporation by reference of documents above is further limited such that no claims included in the documents are incorporated by reference herein. Any incorporation by reference of documents above is yet further limited such that any definitions provided in the documents are not incorporated by reference herein unless expressly included herein.

For purposes of interpreting the claims, it is expressly intended that the provisions of Section 112, sixth paragraph of 35 U.S.C. are not to be invoked unless the specific terms "means for" or "step for" are recited in a claim.

What is claimed is:

1. A pole clamp assembly configured to couple a medical device to a supporting structure, the pole clamp assembly comprising:
- a pole clamp configured to selectively grip the supporting structure, the pole clamp including a fastener hub; and
- a docking member comprising:
  - a hub portion arranged at a proximal end of the docking member and configured to selectively couple to the fastener hub of the pole clamp;
  - a docking member body extending from the proximal end of the docking member to an open distal end, the docking member body including:
    - an elongate projection being configured to be at least partially inserted into a corresponding retaining feature of a medical device, the projection comprising: a bottom surface, a pair of side surfaces, and one or more tabs configured to engage with a corresponding latch of the retaining feature of the medical device,
- wherein the hub portion extends downward from the bottom surface of the projection of the docking member body,
- wherein the pole clamp includes a locking mechanism, wherein the locking mechanism is shiftable between a non-engaged position in which the docking member is rotatable relative to the pole clamp, and an engaged position in which rotation of the docking member relative to the pole clamp is inhibited, and
- wherein the docking member includes at least one recess into which a portion of the locking mechanism can selectively reside therein.

2. The pole clamp assembly of claim 1, wherein the locking mechanism is biased towards the engaged position.

3. The pole clamp assembly of claim 1, wherein the one or more tabs are operably coupled to at least one portion of the at least one side surface.

4. The pole clamp assembly of claim 1, wherein structural support for the projection is in part provided by a keel member extending between structure defining the bottom surface and the top surface.

5. The pole clamp assembly of claim 1, wherein structural support for the projection is in part provided by a lateral rib extending from at least one of the side surfaces.

6. The pole clamp assembly of claim 1, wherein the hub portion further includes a hub face defining a fastener hub aperture and the at least one recess.

7. The pole clamp assembly of claim 6, wherein the hub face defines at least one recess radially arranged around the fastener hub aperture.

8. The pole clamp assembly of claim 6, wherein a longitudinal axis of the docking member body is substantially orthogonal to the hub face.

9. The pole clamp assembly of claim 6, wherein a longitudinal axis of the docking member body is at an obtuse angle relative to the hub face.

10. The pole clamp assembly of claim 6, wherein the hub portion extends downward from a bottom surface of the docking member body such that the entirety of the docking member body is offset outside a bound defined by an outer edge of the hub face.

11. The pole clamp assembly of claim 1, wherein the hub portion is arranged at a proximal end of the docking member, the projection including:
- at least one side surface that is structurally supported by a lateral rib extending from the at least one side surface.

12. The pole clamp assembly of claim 1, wherein the docking member body further includes:
- one or more channels positioned on respective sides of the docking member body and configured to aid in operably coupling the projection with the corresponding retaining feature of the medical device.

13. A pole clamp assembly configured to operably couple a medical device to a supporting structure, the pole clamp assembly comprising:
- a docking member including:
  - a docking member body extending from a first end toward a second end, the second end configured to be at least partially inserted into a corresponding retaining feature of the medical device, the docking member body comprising:
    - a bottom surface and a pair of sidewalls extending therefrom, the docking member body including one or more means for engaging with a retaining feature of the medical device; and
    - one or more docking support ribs coupled with the bottom surface; and
  - a hub portion arranged generally at the first end of the docking member body, and protruding generally orthogonally from the bottom surface, the hub portion including:
    - a hub face having a substantially circular shape and defining one or more recesses surrounding a hub aperture;
    - an outer hub rim extending in a direction opposite the hub face; and
    - a plurality of hub support spokes extending axially outward from proximate the hub aperture to the outer hub rim; and
- a pole clamp having a first side configured to operably couple the docking member and a second side configured to operably couple the supporting structure, the pole clamp comprising:
  - a locking mechanism arranged on the first side, the locking mechanism movable between an engaged position and a disengaged position, wherein:
    - when in the engaged position the locking mechanism selectively engages one of the one or more recesses surrounding the hub aperture such that the selectively engaged recess determines an orientation between the pole clamp and the docking member body and the locking mechanism inhibits rotation of the pole clamp with respect to the docking member body; and
    - when in the disengaged position the pole clamp can be rotated with respect to the docking member body.

* * * * *